United States Patent
Minamoto et al.

(10) Patent No.: US 7,790,409 B2
(45) Date of Patent: Sep. 7, 2010

(54) BLOOD COAGULATION ACCELERATOR AND CONTAINER FOR BLOOD EXAMINATION

(75) Inventors: Masaaki Minamoto, Shunan (JP); Kazuhiko Shimada, Shunan (JP)

(73) Assignee: Sekisui Chemical Co., Ltd., Osaka (JP)

( * ) Notice: Subject to any disclaimer, the term of this patent is extended or adjusted under 35 U.S.C. 154(b) by 499 days.

(21) Appl. No.: 11/663,440

(22) PCT Filed: Mar. 15, 2006

(86) PCT No.: PCT/JP2006/005089

§ 371 (c)(1),
(2), (4) Date: Mar. 21, 2007

(87) PCT Pub. No.: WO2006/098350

PCT Pub. Date: Sep. 21, 2006

(65) Prior Publication Data

US 2008/0274532 A1 Nov. 6, 2008

(30) Foreign Application Priority Data

Mar. 17, 2005 (JP) ............................. 2005-077835

(51) Int. Cl.
*C12Q 1/56* (2006.01)
(52) U.S. Cl. ...................................... 435/13; 435/287.9
(58) Field of Classification Search .................. 435/13, 435/2, 287.9; 436/810; 514/802
See application file for complete search history.

(56) References Cited

U.S. PATENT DOCUMENTS

| 6,458,548 | B2 * | 10/2002 | Kobayashi et al. ............ 435/7.1 |
| 6,979,829 | B2 * | 12/2005 | Calvert et al. ............ 250/472.1 |
| 7,595,028 | B2 * | 9/2009 | Minamoto et al. ........... 422/102 |
| 2003/0133928 | A1 * | 7/2003 | Metzner et al. ........... 424/94.64 |
| 2007/0009578 | A1 * | 1/2007 | Moller et al. ................ 424/443 |

FOREIGN PATENT DOCUMENTS

| JP | 64-40433 A | 2/1989 |
| JP | 2-53732 A | 2/1990 |
| JP | 5-188055 A | 7/1993 |
| JP | 8-154697 A | 6/1996 |
| JP | 10-206420 A | 8/1998 |
| JP | 2001-289843 A | 10/2001 |

* cited by examiner

*Primary Examiner*—Ralph Gitomer
(74) *Attorney, Agent, or Firm*—Sughrue Mion, PLLC

(57) ABSTRACT

The present invention provides a blood coagulation accelerator excellent under severe conditions at ordinary or higher temperatures and capable of exhibiting high blood coagulation performance stably over a long period of time, as well as a container for blood examination wherein the blood coagulation accelerator is accommodated. Disclosed is a blood coagulation accelerator comprising an enzyme capable of hydrolyzing in a peptide chain a bond between arginine and an arbitrary amino acid residue and/or a bond between lysine and an arbitrary amino acid residue, an inactivated enzyme product comprising the above-mentioned enzyme inactivated by radiation irradiation, and β-alanine.

19 Claims, No Drawings

BLOOD COAGULATION ACCELERATOR AND CONTAINER FOR BLOOD EXAMINATION

TECHNICAL FIELD

The present invention relates to a blood coagulation accelerator and a container for blood examination, and in particular, to a blood coagulation accelerator used in clinical examinations such as serum biochemical examination and a container for blood examination in which the blood coagulation accelerator is accommodated.

BACKGROUND ART

In clinical examinations such as serum biochemical examination, a blood coagulation accelerator is used when serum is to be collected from blood in a shorter time, and an enzyme is used as the blood coagulation accelerator. The enzyme used as the blood coagulation accelerator is an enzyme capable of hydrolyzing in a peptide chain a bond between arginine and an arbitrary amino acid residue and/or a bond between lysine and an arbitrary amino acid residue, and thrombin can be mentioned as a typical enzyme. Thrombin has higher blood coagulation activity than that of an inorganic blood coagulation accelerator typified by silica and the like, thus enabling rapid coagulation of blood to give serum in a very short time.

However, thrombin is an unstable enzyme which is hardly stably stored and hardly exhibits a high blood coagulation performance stably over a long period of time. Although lyophilization is conventionally used as a method of stably storing thrombin, this enzyme should be stored in an aluminum package, a glass container or the like and always kept in a suitable storage form to attain stability over a long period of time, and is hardly stably stored when stored particularly in a moisture-permeable container.

In a method of stably storing thrombin in an aqueous solution, for example, an aqueous liquid thrombin composition containing, as a stabilizer, a sugar and an amino acid is disclosed (See Patent document 1). This method is effective in short-term storage at a low temperature, but cannot be applied to a blood coagulation accelerator and a container for blood examination wherein long-term storage stability is required particularly under severe conditions at ordinary or higher temperatures.

As a technique for stabilizing a dry preparation of thrombin, for example, a dry preparation comprising sugars, a basic amino acid and an organic acid salt is disclosed (See Patent document 2).

This dry preparation is effective in low-temperature and short-term storage, but cannot be applied to a blood coagulation accelerator and a container for blood examination wherein long-term storage stability is required particularly under severe conditions at ordinary or higher temperatures. This dry preparation is liable to the influence of humidity and is thus problematic in stability, particularly when stored in a moisture-permeable container.

Patent document 1: JP-A 64-40433
Patent document 2: JP-A 2-53732

DISCLOSURE OF THE INVENTION

The present invention provides a blood coagulation accelerator excellent in long-term storage stability under severe conditions at ordinary or higher temperatures and capable of exhibiting high blood coagulation performance stably over a long period of time, as well as a container for blood examination wherein the blood coagulation accelerator is accommodated.

The blood coagulation accelerator of the present invention comprises an enzyme capable of hydrolyzing in a peptide chain a bond between arginine and an arbitrary amino acid residue and/or a bond between lysine and an arbitrary amino acid residue, an inactivated enzyme product comprising the above enzyme inactivated by radiation irradiation, and $\beta$-alanine.

The blood coagulation accelerator described above has a performance of rapidly coagulating blood and thus simultaneously has a property of changing the blood coagulation performance significantly by a slight difference in activity. When the activity is high, blood is coagulated so rapidly that uneven coagulation may occur to cause precipitation of fibrin in serum after centrifugation. When the activity is low, coagulation of blood is delayed so that necessary serum may not be obtained within a predetermined time. From the viewpoint of qualities, it is preferable that the blood coagulation accelerator always has a constant activity, and it is desired that the blood coagulation accelerator undergoes the minimum change in activity over a period of from immediately after manufacturing to expiration date.

The present invention provides a blood coagulation accelerator excellent in quality and stable with very low fluctuation in activity from immediately after production.

The hydrolyzing enzyme mentioned above includes, for example, serine proteases such as trypsin, thrombin and venom thrombin-like enzyme; thiol proteases such as cathepsin B and ficin; and metal proteases such as kininase, and among which serine proteases are preferable, and particularly thrombin is preferably used. The method of preparing thrombin is not particularly limited, and for example, the enzyme obtained by purification of plasmas from animals (human, bovine and the loke) can be used. Two or more enzymes may also be simultaneously used.

When the amount of the enzyme used in the blood coagulation accelerator of the present invention is decreased, the time required for blood coagulation is too long, while when the amount is increased, blood is coagulated so rapidly that uneven coagulation may occur or an adverse influence on laboratory data may be caused, and thus the amount of the enzyme used, in terms of activity, is preferably 0.1 to 100 IU (International Unit, referred to hereinafter as "U"). For example, when thrombin is used as the enzyme, the amount of thrombin used is preferably 0.5 to 50 U, more preferably 1 to 20 U, per mL of blood.

An inactivated enzyme product comprising the above enzyme inactivated by radiation irradiation, and $\beta$-alanine, is added as the enzyme stabilizer to the blood coagulation accelerator of the present invention. In radiation irradiation, the radiation rays include, for example, gamma rays, electron rays and the like. Two or more inactivated enzyme products may also be simultaneously used.

The amount of the inactivated enzyme product added to the blood coagulation accelerator of the present invention is preferably 0.001 to 100 µg, more preferably 0.01 to 10 µg, most preferably 0.03 to 5 µg, per U of thrombin. Because a large amount of the inactivated enzyme product added is disadvantageous in respect of manufacturing costs, the minimum amount required to achieve the desired performance is preferably used. An inactivated enzyme product inactivated by radiation irradiation may be added as the inactivated enzyme product, or a part of the active enzyme added may be inactivated as the inactivated enzyme product by radiation irradiation.

The amount of the β-alanine added to the blood coagulation accelerator of the present invention is preferably 0.01 to 1000 μg, more preferably 0.1 to 200 μg, most preferably 0.5 to 50 μg, per U of thrombin. When the amount of β-alanine added is high, β-alanine may be hardly dissolved in the blood coagulation accelerator to make the component uneven in the blood coagulation accelerator or to make spray coating of the blood coagulation accelerator impossible, and thus β-alanine is added preferably in such an amount that it can be uniformly dissolved.

In addition to the enzyme described above, an adsorbing inorganic material may also be used in the blood coagulation accelerator of the present invention. For example, the adsorbing inorganic material includes, but is not limited to, silica, kaolin, bentonite, and diatomaceous earth. The adsorbing inorganic material may be accommodated, separately from the enzyme-containing blood coagulation accelerator, in a blood examination container described later, or may be added directly to the blood coagulation accelerator. Two or more adsorbing inorganic materials may also be simultaneously used. The amount of the adsorbing inorganic material used is preferably 0.001 to 10 mg, more preferably 0.01 to 1 mg, per mL of blood.

To prevent blood from adhering to an inner wall of the container for blood examination, a blood clot-releasing component may also be used in the blood coagulation accelerator of the present invention. The blood clot-releasing component includes, for example, silicone oil, polyvinyl pyrrolidone, polyvinyl alcohol, polyoxyalkylene, and derivatives thereof, and these may be used alone or as a mixture of two or more thereof.

As the silicone oil, modified silicone oil of water-soluble type can also be used.

Preferably used polyoxyalkylene and derivatives thereof include, for example, polyoxypropylene butyl ether, polyoxyethylene butyl ether, polyoxypropylene glyceryl ether, polyoxyethylene glyceryl ether, etc.

The blood clot-releasing component may be added directly to the blood coagulation accelerator. The amount of the blood clot-releasing component used is preferably 0.1 μg to 10 mg, more preferably 1 μg to 1 mg, per mL of blood.

An antifibrinolytic agent and/or an antiplasmin agent may be added to the blood coagulation accelerator of the present invention. The antifibrinolytic agent and antiplasmin agent include, for example, aprotinin, soybean trypsin inhibitor, p-aminomethylbenzoic acid, aminomethylcyclohexane carboxylic acid. These compounds may be used alone or as a mixture of two or more thereof. The amount of the antifibrinolytic agent and antiplasmin agent used is preferably 0.1 μg to 10 mg, more preferably 1 μg to 1 mg.

To obtain serum in a short time even from heparin-containing blood from a dialysis patient, a heparin-neutralizing agent may also be used in the blood coagulation accelerator of the present invention. The heparin-neutralizing agent may be added directly to the blood coagulation accelerator. For example, when the blood coagulation-accelerating component in the blood coagulation accelerator is thrombin, the ability of thrombin to coagulate blood is inhibited to fail to coagulate blood where heparin is present in blood. By using the heparin-neutralizing agent simultaneously, heparin in blood is neutralized so that thrombin can exhibit its original blood coagulation ability. The heparin-neutralizing agent includes, for example, an amine salt, a quaternary nitrogen-containing organic compound and protamine sulfate, and at least one of which can be used. The amine constituting the above-mentioned amine salt may be a primary, secondary or tertiary amine, and the acid constituting the amine salt may be either an inorganic or organic acid. The inorganic acid includes, for example, hydrogen halides such as hydrochloric acid and sulfuric acid, sulfurous acid, and the organic acid includes, for example, formic acid and acetic acid. The organic residue of the amine salt is usually an alkyl group but may be a heteroatom-containing hydrocarbon group such as an imino group or an ether group. The amine salt may be an intramolecular salt. Specific examples of the amine salt include, for example, hexadecyldimethylamine hydrochloride and tetradecyl di(aminoethyl)glycine.

The quaternary nitrogen-containing organic compound includes, for example, tetraalkyl ammonium, but may be a compound having an aryl group in place of an alkyl group or a compound having a heteroatom-containing hydrocarbon group such as an imino group or an ether group. Specific examples of the quaternary nitrogen-containing organic compound include, for example, dodecyltrimethyl ammonium chloride. In addition, a quaternary nitrogen-containing organic polymer can also be used. As the organic polymer, a polycation such as polyamine sulfone can be preferably used. A high-molecular-weight polycation is effective for inactivation of heparin and can bind to heparin to insolubilize and precipitate the heparin. The polyamine sulfone includes, for example, a polymer having a repeating unit represented by the following formula (I).

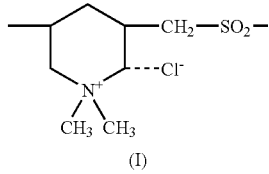

[CHEMICAL 1]

(I)

The polyamine sulfone is a synthetic compound and can thus be handled easily as compared to natural occurring protamine sulfate. It is easily purified and also easily blended in preparing the blood coagulation accelerator. It is also extremely excellent in an ability to neutralize heparin.

The amount of the heparin-neutralizing agent added is suitably determined depending on the amount of heparin contained in blood to be coagulated. For example, when heparin-containing blood from a general dialysis patient is to be coagulated, the amount of the heparin-neutralizing agent is preferably 0.001 to 10 mg, more preferably 0.005 to 1 mg, most preferably 0.01 to 0.5 mg, per mL of blood.

The blood coagulation accelerator of the present invention can be formed into a solution or dispersion in a solvent such as water, and particularly its aqueous solution is preferably used.

The method of accommodating the blood coagulation accelerator in the container for blood examination includes, but is not limited to, a method of dropping an aqueous solution of the blood coagulation accelerator into the container, and a method of applying the blood coagulation accelerator by spraying and the like onto an inner wall of the container. The method of applying the blood coagulation accelerator onto an inner wall of the container is preferably used for effectively coagulating blood.

In consideration of the stability of the enzyme as the blood coagulation accelerator, the blood coagulation accelerator accommodated in the container for blood examination is preferably accommodated in a dried form. The drying method includes, but is not limited to, vacuum drying, heating drying, drying with air such as dehumidified air and heated air, and drying with a desiccant such as silica gel. The blood coagulation accelerator is thus dried and accommodated to improve the storage stability of the blood coagulation accelerator.

The blood coagulation accelerator may be accommodated in a previously dried state, for example, in the form of dried powder or dried granules. In addition, carriers such as a nonwoven fabric, a woven fabric, and a resin or glass sheet or beads may be accommodated in a state having the blood coagulation accelerator carried thereon. In this case, the specific gravity of the carriers is preferably 1.08 or more.

The container for blood examination may be made of synthetic resin or glass, and its material is not particularly limited. The synthetic resin includes, for example, polyethylene, polypropylene, polyethylene terephthalate and polystyrene, and particularly polyethylene terephthalate is preferably used. The container for blood examination made of synthetic resin, even when dropped or impacted, is hardly damaged. Therefore, it is preferable to use the container for blood examination made of synthetic resin in order to prevent blood infection resulting from breakage of the container for blood examination.

The container material is preferably a material excellent in gas barrier property and/or vapor barrier property.

The shape of the container is not particularly limited, and for example, a tubular container having a bottom is preferably used.

The container for blood examination is often used in combination with a stopper. The stoppers include, for example, those made of synthetic resin, elastomer and rubber, and preferable examples of the rubber include, for example, butyl rubber and halogenated butyl rubber. A stopper made of two or more of the above materials may also be used. An example of such stopper is an over-cap-type stopper comprising a rubber or elastomer stopper covered with a cover made of synthetic resin.

A stopper composed of a material excellent in gas barrier property and/or vapor barrier property is preferably used.

The container for blood examination can be produced in the form of a vacuum blood collecting tube depressurized therein. The container in which the blood coagulation accelerator and the like are accommodated may be sealed hermetically with a stopper or the like thereby rendering the container depressurized therein to give a vacuum blood collecting tube. As the container, for example, a tubular container having a bottom is suitably used, and the stopper used is a stopper made of such a material as to keep the inside of the blood examination container in a depressurized state and formed so as to enable pricking for blood collection. The degree of depressurization in the vacuum blood collecting tube is established depending on the amount of blood to be collected.

The method of hermetically sealing the blood collecting tube in a depressurized state with a stopper is not particularly limited. For example, a method wherein the container for blood examination is sealed hermetically by fitting the stopper into the container in a depressurized environment in a vacuum chamber or the like is often used. Alternatively, an opening of the container may be sealed hermetically with, for example, a laminate film consisting of metallic foil.

The container for blood examination can be filled with nitrogen or an inert gas. In particular, nitrogen is preferably used. The inert gas includes, for example, the group XVIII elements such helium, neon and argon. Two or more gases selected from the above-mentioned nitrogen and inert gases may be simultaneously used. The container for blood examination may be filled with the above-mentioned nitrogen and/or inert gases to replace the air in the container for blood examination with the nitrogen and/or inert gases to improve the stability of the enzyme. The method of producing the blood examination container filled with nitrogen and/or an inert gas as a vacuum blood collecting tube comprises, for example, replacing the atmosphere in a vacuum chamber and the loke and in the container for blood examination with nitrogen and/or an inert gas, then depressurizing the system to a predetermined degree of depressurization, and sealing the container hermetically with a stopper.

The container for blood examination can be accommodated and sealed hermetically in a packaging bag made of a gas barrier and/or vapor barrier material.

A deoxidizer and/or a desiccant can be accommodated in the packaging bag. By doing so, it is possible to prevent oxygen and moisture from entering the container for blood examination thereby improving the stability of the enzyme accommodated in the container for blood examination. The desiccant includes, for example, silica gel, zeolite, calcium chloride, calcium oxide and calcium hydroxide. Particularly, silica gel and zeolite are preferably used.

The packaging bag can be filled with nitrogen and/or an inert gas. By doing so, it is possible to prevent oxygen from entering the container for blood examination. In addition, nitrogen and/or an inert gas with which the container for blood examination is filled can be prevented from being replaced, leaked or discharged, and thus the stability of the enzyme accommodated in the container for blood examination is extremely high even upon radiation irradiation or during storage for a long period of time.

This constitution can be used in combination with the constitution of the packaging bag in which the deoxidizer and/or the desiccant is accommodated.

The shape of the packaging bag is not particularly limited insofar as the container for blood examination can be accommodated and sealed hermetically therein. Examples of the packaging bag include a bag sealed on three or four sides, a pouch and a gusseted bag. To minimize the amount of gas or vapor permeating the packaging bag, the inner capacity of the packaging bag is preferably the minimum necessary size in order to reduce the surface area of the packaging bag.

The material of the packaging bag is not particularly limited insofar as it has gas barrier property and/or vapor barrier property. The material of the packaging bag includes, for example, metal foil of aluminum or the like and synthetic resin. The synthetic resin includes, for example, polyethylene, polypropylene, polyethylene terephthalate, nylon, polystyrene, polyvinyl chloride, polyvinylidene chloride, cellophane, an ethylene-vinyl alcohol copolymer. For improving the gas barrier property and/or vapor barrier property or for conferring heat sealing property, a packaging bag constituted by laminating two or more materials through lamination and the like is preferably used. Such packaging bag includes, for example, a packaging bag made of a laminate film consisting of aluminum foil and polyethylene terephthalate or polyethylene.

For example, a packaging bag having the above-mentioned material vapor-deposited with silica, alumina, ceramic or aluminum can also be used. Specific examples include packaging bags comprising a laminate film wherein a film of polyethylene terephthalate or polyethylene vapor-deposited with silica, alumina, ceramic or aluminum is laminated with a heat-sealable film of polyethylene or polypropylene, and such packaging bags can be preferably used. The film vapor-deposited with silica, alumina or ceramic is advantageous in that the film is excellent in gas barrier property and vapor barrier property and also excellent in transparency, the inside of the packaging bag can be visually confirmed, and the packaging bag can be incinerated for disposal. The film vapor-deposited with aluminum is not transparent but has excellent gas barrier property and water vapor barrier property comparative with those of a laminate film of aluminum foil.

Even when the container for blood examination is made of a moisture-permeable material, the blood coagulation accelerator is excellent in storage stability and can exhibit an ability to highly accelerate blood coagulation stably over a long period of time.

For effectively collecting serum for examination, a serum separating agent and the like may be accommodated in the vacuum blood collecting tube. As the serum separating agent, a thixotropic gelatinous material having specific gravity between the specific gravity of serum and that of blood clot is preferably used. After coagulation of blood, the blood is centrifuged such that due to a difference in specific gravity, a partition wall of the serum separating agent is formed between serum and a blood clot thus facilitating the separation of serum.

EFFECT OF THE INVENTION

The blood coagulation accelerator and the container for blood examination according to the present invention are constituted as described above and are excellent in an ability to stabilize the qualities of an enzyme as a blood coagulation-accelerating component. The container for blood examination is particularly excellent when using a moisture-permeable material in storage stability even under severe conditions such as high-temperature and high-humidity conditions and can exhibit an ability to highly accelerate blood coagulation stably over a long period of time.

BEST MODE FOR CARRYING OUT THE INVENTION

Hereinafter, the present invention is described in more detail by reference to Examples, but the present invention is not limited to these.

Example 1

300,000 U thrombin (specific activity of 1500 U/mg, manufactured by Mochida Pharmaceutical Co., Ltd.), 10 mg of an inactivated thrombin product having 10 mg of thrombin (specific activity of 1500 U/mg, manufactured by Mochida Pharmaceutical Co., Ltd.) inactivated by irradiation with gamma rays, and 2 g of β-alanine, were dissolved in 100 g purified water to prepare an aqueous blood coagulation accelerator solution, and 1 g of water-soluble silicone oil was added to the aqueous blood coagulation accelerator solution. 20 μL of the blood coagulation accelerator thus obtained was sprayed into the inside of a polyethylene terephthalate (PET) tubular container (inner diameter 10 mm×length 100 mm) having a bottom and then dried for 12 hours in a vacuum dryer, and the tubular container was hermetically sealed under reduced pressure with a butyl rubber stopper so as to allow blood to be collected in an amount of 5 mL, to give a vacuum blood collecting tube.

Examples 2 to 9

Vacuum blood collecting tubes were obtained in the same manner as in Example 1 except that the amounts of thrombin, the inactivated thrombin product and β-alanine were changed as shown in Table 1.

TABLE 1

|       | Thrombin (in 10 thousands U) | Inactivated Thrombin Product (mg) | β-Alanine (g) |
|-------|------------------------------|-----------------------------------|---------------|
| Ex. 2 | 30                           | 20                                | 2             |
| Ex. 3 | 30                           | 60                                | 2             |
| Ex. 4 | 30                           | 100                               | 2             |
| Ex. 5 | 30                           | 200                               | 2             |
| Ex. 6 | 30                           | 400                               | 2             |
| Ex. 7 | 30                           | 600                               | 2             |
| Ex. 8 | 30                           | 100                               | 0.2           |
| Ex. 9 | 30                           | 100                               | 10            |

Example 10

330,000 U thrombin (specific activity of 1500 U/mg, manufactured by Mochida Pharmaceutical Co., Ltd.) and 2 g of β-alanine were dissolved in 100 g purified water to prepare an aqueous blood coagulation accelerator solution, and 1 g of water-soluble silicone oil was added to the aqueous blood coagulation accelerator solution. 20 μL of the blood coagulation accelerator thus obtained was sprayed into the inside of a polyethylene terephthalate (PET) tubular container (inner diameter 10 mm×length 100 mm) having a bottom and then dried for 12 hours in a vacuum dryer. Thereafter, the tubular container was hermetically sealed under reduced pressure with a butyl rubber stopper so as to allow blood to be collected in an amount of 5 mL, to give a vacuum blood collecting tube. Thereafter, this vacuum blood collecting tube was irradiated with gamma rays to inactivate 6 U of 66 U thrombin contained in the blood coagulation accelerator in one vacuum blood collecting tube to afford an inactivated thrombin product (corresponding to 4 μg). In this manner, the vacuum blood collecting tube in which a blood coagulation accelerator comprising 60 U thrombin, 4 μg inactivated thrombin product, 0.4 mg β-alanine and 0.2 mg water-soluble silicone oil had been accommodated was obtained.

Example 11

360,000 U thrombin (specific activity of 1500 U/mg, manufactured by Mochida Pharmaceutical Co., Ltd.) and 2 g of β-alanine were dissolved in 100 g purified water to prepare an aqueous blood coagulation accelerator solution, and 1 g of water-soluble silicone oil was added to the aqueous blood coagulation accelerator solution. 20 μL of the blood coagulation accelerator thus obtained was sprayed into the inside of a polyethylene terephthalate (PET) tubular container (inner diameter 10 mm×length 100 mm) having a bottom and then dried for 12 hours in a vacuum dryer. Thereafter, the tubular container was hermetically sealed under reduced pressure with a butyl rubber stopper so as to allow blood to be collected in an amount of 5 mL, to give a vacuum blood collecting tube. Thereafter, this vacuum blood collecting tube was irradiated with electron rays to inactivate 12 U of 72 U thrombin contained in the blood coagulation accelerator in one vacuum blood collecting tube to afford an inactivated thrombin product (corresponding to 8 μg). In this manner, the vacuum blood collecting tube in which a blood coagulation accelerator comprising 60 U thrombin, 8 µg inactivated thrombin product, 0.4 mg β-alanine and 0.2 mg water-soluble silicone oil had been accommodated was obtained.

Example 12

300,000 U thrombin (specific activity of 1500 U/mg, manufactured by Mochida Pharmaceutical Co., Ltd.), 20 mg of an inactivated thrombin product having 20 mg of thrombin (specific activity of 1500 U/mg, manufactured by Mochida Pharmaceutical Co., Ltd.) inactivated by irradiation with gamma rays, and 2 g of β-alanine, were dissolved in 100 g purified water to prepare an aqueous blood coagulation accelerator solution, and 1 g of water-soluble silicone oil was added to the aqueous blood coagulation accelerator solution. 20 µL of the blood coagulation accelerator thus obtained was sprayed into the inside of a polyethylene terephthalate (PET) tubular container (inner diameter 10 mm×length 100 mm) having a bottom and then dried for 12 hours in a vacuum dryer. Thereafter, the atmosphere in the vacuum chamber and in the tubular container having a bottom was replaced with nitrogen, and the tubular container was hermetically sealed under reduced pressure with a butyl rubber stopper so as to allow blood to be collected in an amount of 5 mL, to give a vacuum blood collecting tube.

Example 13

A vacuum blood collecting tube was obtained in the same manner as in Example 12 except that replacement with helium was used in place of replacement with nitrogen.

Example 14

A vacuum blood collecting tube was obtained in the same manner as in Example 4 except that polyvinyl pyrrolidone was used in place of water-soluble silicone oil.

Example 15

A vacuum blood collecting tube was obtained in the same manner as in Example 4 except that polyvinyl alcohol was used in place of water-soluble silicone oil.

Example 16

A vacuum blood collecting tube was obtained in the same manner as in Example 4 except that polyoxypropylene glyceryl ether was used in place of water-soluble silicone oil.

Example 17

300,000 U thrombin (specific activity of 1500 U/mg, manufactured by Mochida Pharmaceutical Co., Ltd.), 20 mg of an inactivated thrombin product having 20 mg of thrombin (specific activity of 1500 U/mg, manufactured by Mochida Pharmaceutical Co., Ltd.) inactivated by irradiation with gamma rays, and 2 g of β-alanine, were dissolved in 100 g purified water to prepare an aqueous blood coagulation accelerator solution, and 1 g of water-soluble silicone oil and 3 g of silica were added to the aqueous blood coagulation accelerator solution. 20 µL of the blood coagulation accelerator thus obtained was sprayed into the inside of a polyethylene terephthalate (PET) tubular container (inner diameter 10 mm×length 100 mm) having a bottom and then dried for 12 hours in a vacuum dryer, and the tubular container was hermetically sealed under reduced pressure with a butyl rubber stopper so as to allow blood to be collected in an amount of 5 mL, to give a vacuum blood collecting tube.

Example 18

300,000 U thrombin (specific activity of 1500 U/mg, manufactured by Mochida Pharmaceutical Co., Ltd.), 20 mg of an inactivated thrombin product having 20 mg of thrombin (specific activity of 1500 U/mg, manufactured by Mochida Pharmaceutical Co., Ltd.) inactivated by irradiation with gamma rays, and 2 g of β-alanine, were dissolved in 100 g purified water to prepare an aqueous blood coagulation accelerator solution, and 1 g of water-soluble silicone oil was added to the aqueous blood coagulation accelerator solution. 20 mg of the blood coagulation accelerator thus obtained was coated onto the surface of polyethylene terephthalate beads (specific gravity 1.4) and the beads were accommodated in a polyethylene terephthalate (PET) tubular container (inner diameter 10 mm×length 100 mm) having a bottom, and the tubular container was hermetically sealed under reduced pressure with a butyl rubber stopper so as to allow blood to be collected in an amount of 5 mL, to give a vacuum blood collecting tube.

Example 19

300,000 U thrombin (specific activity of 1500 U/mg, manufactured by Mochida Pharmaceutical Co., Ltd.), 100 mg of an inactivated thrombin product having 100 mg of thrombin (specific activity of 1500 U/mg, manufactured by Mochida Pharmaceutical Co., Ltd.) inactivated by irradiation with gamma rays, 2 g of β-alanine, and 0.5 g of polyamine sulfone represented by formula (I) below as a quaternary nitrogen-containing organic compound were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

[CHEMICAL 1]

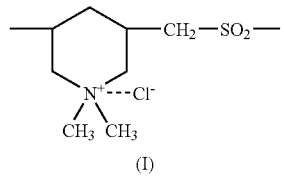

(I)

Example 20

300,000 U thrombin (specific activity of 1500 U/mg, manufactured by Mochida Pharmaceutical Co., Ltd.), 20 mg of an inactivated thrombin product having 20 mg of thrombin (specific activity of 1500 U/mg, manufactured by Mochida Pharmaceutical Co., Ltd.) inactivated by irradiation with gamma rays, 2 g of β-alanine, and 1 g of hexadecyldimethylamine hydrochloride were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Example 21

300,000 U thrombin (specific activity of 1500 U/mg, manufactured by Mochida Pharmaceutical Co., Ltd.), 600 mg of an inactivated thrombin product having 600 mg of thrombin (specific activity of 1500 U/mg, manufactured by Mochida Pharmaceutical Co., Ltd.) inactivated by irradiation with gamma rays, 2 g of β-alanine, and 2 g of protamine sulfate were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Example 22

100 vacuum blood collecting tubes obtained in Example 4 and 20 g silica gel were accommodated in a gusseted bag (bag underside: 120×300 mm) consisting of a laminate film having PET/alumina vapor-deposited PET/polyethylene laminated therein, and the air in the bag was removed to the maximum degree by vacuum suction, and the gusseted bag was heat-sealed in a position at a height of 250 mm from the bottom to seal the bag hermetically.

Example 23

100 vacuum blood collecting tubes obtained in Example 12 and 20 g silica gel were accommodated in a gusseted bag (bag underside: 120×300 mm in dimension) consisting of a laminate film having PET/alumina vapor-deposited PET/polyethylene laminated therein, and the air in the bag was removed to the maximum degree by vacuum suction, and the gusseted bag was heat-sealed in a position at a height of 250 mm from the bottom to seal the bag hermetically.

Example 24

100 vacuum blood collecting tubes obtained in Example 12 and a deoxidizer were accommodated in a gusseted bag (bag underside: 120×300 mm in dimension) consisting of a laminate film having PET/alumina vapor-deposited PET/polyethylene laminated therein, and the air in the bag was removed to the maximum degree by vacuum suction, and the gusseted bag was heat-sealed in a position at a height of 250 mm from the bottom to seal the bag hermetically.

Example 25

100 vacuum blood collecting tubes obtained in Example 12 were accommodated in a gusseted bag (bag underside: 120×300 mm in dimension) consisting of a laminate film having PET/silica vapor-deposited PET/polyethylene laminated therein, and after the air in the bag was replaced with nitrogen, the gusseted bag was heat-sealed in a position at a height of 250 mm from the bottom to seal the bag hermetically.

Example 26

100 vacuum blood collecting tubes obtained in Example 13 were accommodated in a gusseted bag (bag underside: 120×300 mm in dimension) consisting of a laminate film having PET/Al/nylon/polypropylene laminated therein, and after the air in the bag was replaced with helium, the gusseted bag was heat-sealed in a position at a height of 250 mm from the bottom to seal the bag hermetically.

Comparative Example 1

300,000 U thrombin (specific activity of 1500 U/mg, manufactured by Mochida Pharmaceutical Co., Ltd.) was dissolved in 100 g purified water to prepare an aqueous blood coagulation accelerator solution, and 1 g of water-soluble silicone oil was added to the aqueous blood coagulation accelerator solution. From the blood coagulation accelerator solution thus obtained, a vacuum blood collecting tube was obtained in the same manner as in Example 1.

Comparative Example 2

300,000 U thrombin (specific activity of 1500 U/mg, manufactured by Mochida Pharmaceutical Co., Ltd.) and 2 g of β-alanine were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Comparative Example 3

300,000 U thrombin (specific activity of 1500 U/mg, manufactured by Mochida Pharmaceutical Co., Ltd.) and 10 g of β-alanine were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Comparative Example 4

300,000 U thrombin (specific activity of 1500 U/mg, manufactured by Mochida Pharmaceutical Co., Ltd.), and 20 mg of an inactivated thrombin product having 20 mg of thrombin (specific activity of 1500 U/mg, manufactured by Mochida Pharmaceutical Co., Ltd.) inactivated by irradiation with gamma rays, were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Comparative Example 5

300,000 U thrombin (specific activity of 1500 U/mg, manufactured by Mochida Pharmaceutical Co., Ltd.), and 200 mg of an inactivated thrombin product having 200 mg of thrombin (specific activity of 1500 U/mg, manufactured by Mochida Pharmaceutical Co., Ltd.) inactivated by irradiation with gamma rays, were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Comparative Example 6

300,000 U thrombin (specific activity of 1500 U/mg, manufactured by Mochida Pharmaceutical Co., Ltd.), 20 mg of an inactivated thrombin product having 20 mg of thrombin (specific activity of 1500 U/mg, manufactured by Mochida Pharmaceutical Co., Ltd.) inactivated by irradiation with gamma rays, and 2 g of α-alanine in place of β-alanine, were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

Comparative Example 7

300,000 U thrombin (specific activity of 1500 U/mg, manufactured by Mochida Pharmaceutical Co., Ltd.), 20 mg of an inactivated thrombin product having 20 mg of thrombin (specific activity of 1500 U/mg, manufactured by Mochida Pharmaceutical Co., Ltd.) inactivated by irradiation with gamma rays, and 2 g of glycine, were dissolved in 100 g purified water to prepare an aqueous blood coagulation accelerator solution, and 1 g of water-soluble silicone oil was added to the aqueous blood coagulation accelerator solution. From the blood coagulation accelerator thus obtained, a vacuum blood collecting tube was obtained in the same manner as in Example 1.

The vacuum blood collecting tubes obtained in the Examples and Comparative Examples were stored in a constant-temperature/constant-humidity (35° C./75% RH) chamber and measured for their thrombin activity (residual ratio relative to the activity just after production) just after production, after storage for 2 weeks and after storage for 1 month to evaluate stability. This evaluation was carried out for each vacuum blood collecting tube just after production.

The vacuum blood collecting tubes just after production, after storage for 2 weeks and after storage for 1 month respectively were used to vacuum-collect 5 mL blood from a healthy person, and by falling upside down rapidly and gently 5 times, the blood was mixed with the blood coagulation accelerator, left for 5 minutes and then centrifuged. Generation of fibrin in serum and serum yield were observed. The results are shown in Table 2.

TABLE 2

|  | Residual ratio of thrombin activity (%) | | | Generation of Fibrin | | | Serum Yield | | |
| --- | --- | --- | --- | --- | --- | --- | --- | --- | --- |
|  | Just After Production | After 2 Weeks | After 1 Month | Just After Production | After 2 Weeks | After 1 Month | Just After Production | After 2 Weeks | After 1 Month |
| Ex. 1 | 100 | 81 | 70 | ○ | ○ | ○ | ○ | ○ | ○ |
| Ex. 2 | 100 | 85 | 74 | ○ | ○ | ○ | ○ | ○ | ○ |
| Ex. 3 | 100 | 88 | 78 | ○ | ○ | ○ | ○ | ○ | ○ |
| Ex. 4 | 100 | 89 | 80 | ○ | ○ | ○ | ○ | ○ | ○ |
| Ex. 5 | 100 | 90 | 82 | ○ | ○ | ○ | ○ | ○ | ○ |
| Ex. 6 | 100 | 93 | 85 | ○ | ○ | ○ | ○ | ○ | ○ |
| Ex. 7 | 100 | 94 | 89 | ○ | ○ | ○ | ○ | ○ | ○ |
| Ex. 8 | 100 | 86 | 77 | ○ | ○ | ○ | ○ | ○ | ○ |
| Ex. 9 | 100 | 90 | 84 | ○ | ○ | ○ | ○ | ○ | ○ |
| Ex. 10 | 100 | 87 | 76 | ○ | ○ | ○ | ○ | ○ | ○ |
| Ex. 11 | 100 | 84 | 75 | ○ | ○ | ○ | ○ | ○ | ○ |
| Ex. 12 | 100 | 93 | 90 | ○ | ○ | ○ | ○ | ○ | ○ |
| Ex. 13 | 100 | 92 | 90 | ○ | ○ | ○ | ○ | ○ | ○ |
| Ex. 14 | 100 | 87 | 79 | ○ | ○ | ○ | ○ | ○ | ○ |
| Ex. 15 | 100 | 88 | 80 | ○ | ○ | ○ | ○ | ○ | ○ |
| Ex. 16 | 100 | 90 | 82 | ○ | ○ | ○ | ○ | ○ | ○ |
| Ex. 17 | 100 | 83 | 72 | ○ | ○ | ○ | ○ | ○ | ○ |
| Ex. 18 | 100 | 91 | 83 | ○ | ○ | ○ | ○ | ○ | ○ |
| Ex. 19 | 100 | 90 | 79 | ○ | ○ | ○ | ○ | ○ | ○ |
| Ex. 20 | 100 | 87 | 77 | ○ | ○ | ○ | ○ | ○ | ○ |
| Ex. 21 | 100 | 92 | 88 | ○ | ○ | ○ | ○ | ○ | ○ |
| Ex. 22 | 100 | 96 | 92 | ○ | ○ | ○ | ○ | ○ | ○ |
| Ex. 23 | 100 | 98 | 96 | ○ | ○ | ○ | ○ | ○ | ○ |
| Ex. 24 | 100 | 96 | 92 | ○ | ○ | ○ | ○ | ○ | ○ |
| Ex. 25 | 100 | 97 | 94 | ○ | ○ | ○ | ○ | ○ | ○ |
| Ex. 26 | 100 | 96 | 93 | ○ | ○ | ○ | ○ | ○ | ○ |
| Comp. Ex. 1 | 100 | 23 | 0 | ○ | X | X | ○ | X | X |
| Comp. Ex. 2 | 100 | 68 | 39 | ○ | X | X | ○ | ○ | X |
| Comp. Ex. 3 | 100 | 68 | 42 | ○ | X | X | ○ | ○ | X |
| Comp. Ex. 4 | 100 | 37 | 0 | ○ | X | X | ○ | X | X |
| Comp. Ex. 5 | 100 | 39 | 0 | ○ | X | X | ○ | X | X |
| Comp. Ex. 6 | 100 | 35 | 0 | ○ | X | X | ○ | X | X |
| Comp. Ex. 7 | 100 | 47 | 12 | ○ | X | X | ○ | X | X |

Generation of Fibrin: ○ Fibrin was not generated; X Fibrin was generated
Serum yield: ○ 30% or more relative to the amount of blood collected; X Less than relative to the amount of blood collected Separately, 5 mL heparin-containing blood, that is, blood to which 1 U heparin had been added per mL of blood, was added to each of the vacuum blood collecting tubes in Examples 19, 20 and 21 (just after production, after 2 weeks, and after 1 month), and by falling upside down rapidly and gently 5 times, the blood was mixed with the blood coagulation accelerator. As a result, the blood in any vacuum blood collecting tubes just after production, after 2 weeks, and after 1 month was coagulated within 5 minutes and could, upon centrifugation, give 2 mL or more serum without precipitation of fibrin. The blood in each of the vacuum blood collecting tubes in the other examples and comparative examples, even when left for 1 hour after blood was added and being mixed with the blood coagulation accelerator by falling upside down, was not coagulated.

The invention claimed is:

1. A blood coagulation accelerator comprising an enzyme having peptide chain hydrolyzing activity at least between arginine and another amino acid residue or between lysine and another amino acid residue, an inactivated enzyme product comprising said enzyme inactivated by irradiation with gamma rays or electron rays, and β-alanine.

2. The blood coagulation accelerator according to claim 1, which comprises 0.01 to 10 μg of the inactivated enzyme product comprising said enzyme inactivated by irradiation and 0.1 to 200 μg of β-alanine, per U of the activity of said enzyme.

3. The blood coagulation accelerator according to claim 1, wherein the enzyme is thrombin.

4. The blood coagulation accelerator according to claim 1, which further comprises at least one member selected from the group consisting of silicone oil, polyvinyl pyrrolidone, polyvinyl alcohol, polyoxyalkylene and a derivative thereof.

5. The blood coagulation accelerator according to claim 1, which further comprises at least one member selected from an amine salt, a quaternary nitrogen-containing organic compound, and protamine sulfate.

6. The blood coagulation accelerator according to claim 1, which further comprises an adsorbing inorganic material.

7. The blood coagulation accelerator according to claim 1, which comprises 0.01 to 10 μg of the inactivated enzyme product comprising said enzyme inactivated by irradiation and 0.1 to 200 μg of β-alanine, per U of the activity of said enzyme;
wherein the enzyme is thrombin;
and which further comprises at least one member selected from the group consisting of silicone oil, polyvinyl pyrrolidone, polyvinyl alcohol, polyoxyalkylene and a derivative thereof.

8. The blood coagulation accelerator according to claim 1, which comprises 0.01 to 10 μg of the inactivated enzyme product comprising said enzyme inactivated by irradiation and 0.1 to 200 μg of β-alanine, per U of the activity of said enzyme;
wherein the enzyme is thrombin;
and which further comprises at least one member selected from the group consisting of silicone oil, polyvinyl pyrrolidone, polyvinyl alcohol, polyoxyalkylene and a derivative thereof;
and which further comprises an absorbing inorganic material.

9. The blood coagulation accelerator according to claim 1, which comprises 0.01 to 10 μg of the inactivated enzyme product comprising said enzyme inactivated by irradiation and 0.1 to 200 μg of β-alanine, per U of the activity of said enzyme;
wherein the enzyme is thrombin;
and which further comprises at least one member selected from the group consisting of silicone oil, polyvinyl pyrrolidone, polyvinyl alcohol, polyoxyalkylene and a derivative thereof;
and which further comprises at least one member selected from an amine salt, a quaternary nitrogen-containing organic compound, and protamine sulfate; and which further comprises an adsorbing inorganic material.

10. A container for blood examination accommodating a blood coagulation accelerator comprising an enzyme having peptide chain hydrolyzing activity at least between arginine and another amino acid residue or between lysine and another amino acid residue, an inactivated enzyme product comprising said enzyme inactivated by irradiation with gamma rays or electron rays, and β-alanine.

11. The container for blood examination according to claim 10, which has the blood coagulation accelerator applied to an inner wall thereof.

12. The container for blood examination according to claim 10, wherein a carrier having a specific gravity of 1.08 or more having the blood coagulation accelerator applied thereon is accommodated.

13. The container for blood examination according to claim 10, wherein the blood coagulation accelerator is accommodated in a dried form.

14. The container for blood examination according to claim 10, wherein the blood coagulation accelerator is accommodated in a tubular container having a bottom, and the tubular container is hermetically sealed with a sealable stopper and depressurized therein.

15. The container for blood examination according to claim 10, wherein the container for blood examination is further filled with nitrogen and/or an inert gas.

16. The container for blood examination according to claim 10, wherein the container for blood examination is made of synthetic resin.

17. The container for blood examination according to claim 10, wherein the container for blood examination is hermetically sealed in a packaging bag consisting of a gas barrier and/or vapor barrier material.

18. The container for blood examination according to claim 17, wherein a deoxidizer and/or a desiccant is accommodated in the packaging bag.

19. The container for blood examination according to claim 17, wherein the packaging bag is filled with nitrogen and/or an inert gas.

* * * * *